(12) United States Patent
Eutick

(10) Patent No.: US 10,160,735 B2
(45) Date of Patent: Dec. 25, 2018

(54) PROCESS FOR THE PURIFICATION OF DIAMINOPHENOTHIAZINIUM COMPOUNDS

(71) Applicant: EUPHARMA PTY LTD, Northbridge New South Wales (AU)

(72) Inventor: Malvin Eutick, Northbridge New South Wales (AU)

(73) Assignee: Eupharma Pty Ltd, Northbridge New South Wales (AU)

( * ) Notice: Subject to any disclaimer, the term of this patent is extended or adjusted under 35 U.S.C. 154(b) by 0 days.

(21) Appl. No.: 15/615,225

(22) Filed: Jun. 6, 2017

(65) Prior Publication Data

US 2017/0267652 A1    Sep. 21, 2017

Related U.S. Application Data

(63) Continuation-in-part of application No. 14/911,813, filed as application No. PCT/AU2014/000807 on Aug. 15, 2014, now Pat. No. 9,701,648.

(30) Foreign Application Priority Data

Aug. 15, 2013    (AU) ................................ 2013903099

(51) Int. Cl.
  *C07D 279/22*    (2006.01)
  *B01D 9/02*    (2006.01)
  *A61K 31/5415*    (2006.01)
  *C09B 21/00*    (2006.01)

(52) U.S. Cl.
  CPC ........ *C07D 279/22* (2013.01); *A61K 31/5415* (2013.01); *B01D 9/02* (2013.01); *C09B 21/00* (2013.01)

(58) Field of Classification Search
  CPC .................................................... C07D 279/22
  USPC .......................................................... 544/36
  See application file for complete search history.

(56) References Cited

U.S. PATENT DOCUMENTS

2009/0291943 A1    11/2009    Feraud et al.

FOREIGN PATENT DOCUMENTS

GB         1 293 757      10/1972
WO    WO 2006/032879      3/2006

*Primary Examiner* — Kahsay Habte
(74) *Attorney, Agent, or Firm* — Womble Bond Dickinson (US) LLP

(57) ABSTRACT

A process for the purification of diaminophenothiazinium compounds, and particularly of methylene blue, is described. The process provides for simple and effective purification by reduction of the post-synthesis or commercially available diaminophenothiazinium compound to form a reduced complex thereof. This can then be purified in a more straightforward manner than the original compound by, for example, recrystallization before being allowed to oxidize back to the diaminophenothiazinium compound.

16 Claims, No Drawings

PROCESS FOR THE PURIFICATION OF DIAMINOPHENOTHIAZINIUM COMPOUNDS

CROSS-REFERENCE TO RELATED APPLICATIONS

The present application is a Continuation-in-Part of U.S. patent application Ser. No. 14/911,813, filed Feb. 12, 2016, which is a U.S. National Stage of International Patent Application PCT/AU2014/000807, filed Aug. 15, 2014, and claims priority to Australian Patent Application No. 2013903099, filed Aug. 15, 2013, the disclosures of which are incorporated herein by reference in their entirety

FIELD OF THE INVENTION

The invention relates to the purification of diaminophenothiazinium compounds and novel diaminophenothiazinium compounds formed during the purification process. In particular, the invention relates, but is not limited, to the purification of methylene blue and closely related compounds using novel intermediate complexes.

BACKGROUND TO THE INVENTION

Any reference to background art herein is not to be construed as an admission that such art constitutes common general knowledge in Australia or elsewhere.

The diaminophenothiazinium dyes are well known. In particular, the medical dye or antidote, methylthioninium chloride (3,7-bis (dimethylamino) phenothiazin-5-ylium chloride), known commonly as "methylene blue", has in relatively recent times extended its use to a number of medical applications beyond its historic uses. Other common names for this dye include tetramethylthionine chloride, C.I. Solvent Blue, Swiss Blue, C.I. Basic Blue 8, Aniline Violet and Urolene Blue. It has the following structure (Formula I), although a person of skill in the art will appreciate the existence of certain resonance structures and tautomeric forms:

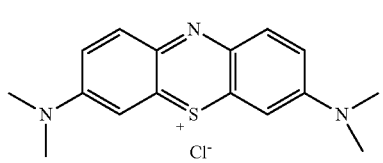

FORMULA I

Methylene blue has a long history of varied uses. Industrial applications have included its use as a colouring agent, redox indicator and dye, an immunological or microbiological stain, in photoelectronic imaging, as an environmental metal sequestrant, a leather dye and an antiseptic.

In the clinical field it has two primary established uses: firstly, as an antidote for methaemoglobinaemia, and occasionally for cyanide and carbon monoxide poisoning, and, secondly, as a chromodiagnostic or chromoendoscopic agent for a wide variety of clinical conditions, such as examining cellular dysplasia in for example Barret's Oesphagous and endoscopic polypectomy, and Fallopian tube patency and Fistula detection.

In 1891 Paul Ehrlich identified methylene blue as a treatment for Malaria. More recently it has been suggested that its use may be broadened to include treatment of tauropathies (or neurodegenerative diseases), viral infections, bipolar disorder and tracing of lymph nodes and lymphatic drainage. In dentistry, uses include finding small cracks in teeth and as a photodynamic dye for treating chronic peridontitis. Methylene blue is added to bone cements to provide discrimination between native and synthetic bone. It has also been used as an accelerant to harden bone cement, effectively increasing the speed at which the bone cement can be effectively applied. In species other than human, it has a wide range of uses, from treating "fin rot" in aquarium fish to methaemoglobinaemia in farm dogs caused by their inadvertent ingestion of toxic fox baits.

The original synthesis of methylene blue was developed in Germany in 1877 (German patent No. 1886 to Badische Anilin-und Soda Fabrik) and since that time a number of other methodologies have been described or patented. A common thread to all the methodologies is the use of a range of metal catalysts including salts (or the metals themselves) of iron, manganese, copper, chromium (as chromate), aluminium and zinc, leaving a potential for metal ion contamination from the catalyst. Further metal contamination may come from the types of metal equipment used for the synthetic processes.

In addition to metal residues, the chemistry of methylene blue lends itself, during production, to the synthesis or inter-conversion of three other structurally and chemically similar organic entities. While these may have little effect on the industrial uses of methylene blue, and may also be used for similar cytological staining purposes, in clinical use these may be considered as undesired inclusions and are specifically cited in the United States Pharmacopoeia (USP) and British/European Pharmacopoeia (BP/EP) as contaminants.

These organic contaminants are collectively called "Azures" and come from some level of demethylation of the two dimethylamino groups at the 3 and 5 positions on the ring structure of methylene blue. Specifically they are: the trimethyl derivative known as Azure B (FORMULA II); the dimethyl derivative known as Azure A (FORMULA III) and monomethyl derivative known as Azure C (FORMULA IV).

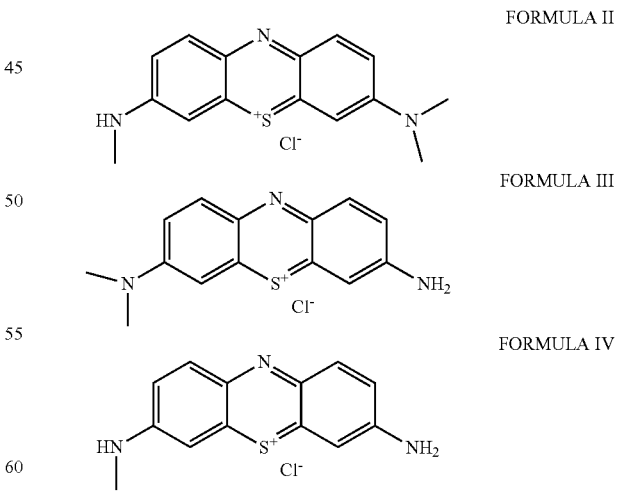

Due to the structural and chemical similarity of the Azures to methylene blue, these 'contaminants' are difficult to separate or remove from a mixture by standard means. It has also proven to be difficult to reduce their occurrence during synthesis of methylene blue. Nevertheless, numerous attempts have been made to remove or reduce the levels of Azures during the synthetic process, including re-purification by many means including recrystallization of the final methylene blue product itself. Marshall and Lewis (1975) describe the purification of commercial methylene blue and Azure B by solvent extraction at a high pH of 9.5 with carbon tetrachloride and subsequent recrystallization. They also describe metal ion removal by low temperature, low pH crystallisation. Lohr et al (1975) describe a purification process utilising column ion chromatography which is not practicable on a commercial scale.

More recently, in 2005 Storey et al (WO 2006/032879) described processes for the de novo manufacture and purification of methylene blue and derivatives thereof using a number of metal ions as catalysts within stepped processes (including chromate (IV) and copper (II) sulphate and iron (II) oxide) under controlled pH and temperature conditions. This is followed by washing/solvent extraction with organic solvents such as dichloromethane, 1,2-dichloroethane, chloroform, ethyl acetate, diethyl ether, chlorobenzene, petroleum ether, benzene, toluene and methyl acetate. Key steps in the final stage of the process include the addition of dimethyldithiocarbamate (DT), a sulphide, and a chloride salt such as sodium chloride, and carbonate such as sodium carbonate followed again by organic solvent washing and the addition of EDTA (ethylenediaminetetraacetic acid), followed again by organic solvent washing and recrystallization and washing at a low pH in the presence of an organic solvent such as dichloromethane or tetrahydrofuran.

Further work by the same group (WO 2008/007074) describes purification of methylene blue by acyl derivatization, at the N10 position (or a number of other organic derivatives including saturated aliphatic derivatives) and purification (with agents such as activated charcoal) and conversion by oxidation to the original methylene blue. The document also includes the concept of acylating a methylene blue precursor and purifying via the same processes.

A number of authors, in a similar fashion, have postulated that metal and organic residue removal may be achieved by further derivatization of the methylene blue, post manufacture, so as to increase the chemical differences between the Azures and methylene blue and also to allow ease of metal residue removal. Buc et al 1959 (U.S. Pat. No. 2,909,520) described processes for the manufacture of acylated leuco methylene blue, in particular benzoyl leuco methylene blue.

Gensler et al, 1966, describes the simple oxidative re-conversion of N-benzoyl leuco methylene blue to methylene blue. In fact all that was required was the presence of oxygen for an autoconversion.

Feraud et al (WO2008/006979) describe a method for industrial purification of methylene blue and other like compounds where both the Azures and metal levels are alleged to be reduced based on the formation of a large organic derivative of methylene blue by reaction to form a N—C bond at the N10 position of a diaminophenothiazinium compound.

This complex multi-step derivatization of methylene blue (or a related derivative thereof) begins with reduction of the N followed by reaction of the resulting amine with certain derivative options. They then proceed to describe standard methods and/or concepts for purification of the complex organic derivative, including reduction of metal ion levels via filtration of the derivatized organic material through a support that retains metals, crystallisation from an appropriate solvent and other known methods. They use solvent washing or recrystallization to reduce the Azure levels in this derivative. Again, the final process is reconversion or oxidation to methylene blue using quinones, nitric acid, perchloric acid iodine, hydrochloric acid, sulphuric acid, hydrogen peroxide or UV light, with a preference for 2,3-dichloro-5,6-dicyano-1,4-benzoquinone (DDQ).

In summary, the levels of metals and/or organic impurities found within methylene blue samples is not unexpected when such historic synthetic approaches are considered, and may even be acceptable for the commercial product in use for many industrial and cytological purposes where these potential residues do not affect the use. However, with recent requirements for lower levels of these impurities in methylene blue used for pharmaceutical purposes, it has become necessary to address the removal of impurities in an efficient, simple and cost effective purification process.

OBJECT OF THE INVENTION

It is an aim of this invention to provide a purification method and intermediate which overcomes or ameliorates one or more of the disadvantages or problems described above, or which at least provides a useful alternative or simpler methodology.

Other preferred objects of the present invention will become apparent from the following description.

SUMMARY OF INVENTION

According to a first aspect of the invention, there is provided a process for the purification of a diaminophenothiazinium compound including the steps of:
  (i) contacting the diaminophenothiazinium compound with a carbocyclic or heterocyclic reducing agent to form a protonated stabilised diaminophenothiazinium complex;
  (ii) purifying the protonated stabilised diaminophenothiazinium complex and;
  (iii) contacting the purified protonated stabilised diaminophenothiazinium complex with an oxidising agent to convert it back to the diaminophenothiazinium compound,
to thereby purify the diaminophenothiazinium compound.

The diaminophenothiazinium compound may be selected from the group consisting of methylene blue, Azure A, Azure B and Azure C.

In one embodiment, the contact with the reducing agent may form an N-10 protonated stabilised diaminophenothiazinium complex which is subsequently purified and oxidised back to the diaminophenothiazinium compound.

In one preferred embodiment of the first aspect, there is provided a process for the purification of methylene blue including the steps of:
  (i) contacting the methylene blue with a carbocyclic or heterocyclic reducing agent to form a stabilised protonated leucomethylene blue complex;
  (ii) purifying the stabilised protonated leucomethylene blue complex; and
  (iii) contacting the purified stabilised protonated leucomethylene blue complex with an oxidising agent to form methylene blue,
to thereby purify the methylene blue.

The reducing agent of the first aspect, and the preferred embodiment thereof, is a metal-free carbocyclic or heterocyclic reducing agent.

In embodiments, the heterocyclic reducing agent is selected from a reducing sugar, a sugar acid or a salt of either.

Suitable salt forms of the reducing sugar or sugar acid may be selected from sodium, calcium, potassium, magnesium, ammonium and lithium salts.

In certain embodiments, when the reducing agent is a heterocyclic reducing agent it comprises a C5 or C6 oxygen-containing ring. Such ring systems include pyran and furan rings which may be optionally substituted. Preferred ring systems are reducing sugars, or sugar acids such as ascorbic acid and its isomers.

In embodiments, when the reducing agent is a carbocyclic reducing agent it may be hydroquinone.

In one embodiment, the reducing agent of the first aspect, and the preferred embodiment thereof, is selected from the group consisting of D-ascorbic acid, L-ascorbic acid, D-isoascorbic acid, L-isoascorbic acid, fructose, dextrose, lactose, xylitol and salts thereof.

Suitably, the reducing agent of the first aspect, and the preferred embodiment thereof, is ascorbic acid or a salt or isomer thereof. Preferably it is L-ascorbic acid or a salt thereof.

In any embodiment described herein, the reducing agent may be a monosaccharide reducing agent.

Preferably, the diaminophenothiazinium compound or methylene blue is contacted with the reducing agent at an acidic pH. More preferably, the diaminophenothiazinium compound or methylene blue is contacted with the reducing agent at below pH 3. Even more preferably, the diaminophenothiazinium compound or methylene blue is contacted with the reducing agent at below pH 1.

Preferably, the reducing agent is in a solution made acidic with an acid chosen from a monoprotic or diprotic mineral acid.

Suitably, the acid is selected from the group consisting of hydrochloric, sulphuric, nitric, phosphoric, boric, hydrofluoric, hydrobromic and perchloric acids.

In one embodiment, the mineral acid is hydrochloric or sulphuric acid.

Suitably, the mineral acid is hydrochloric acid.

Preferably, the contacting with the reducing agent of the first aspect, and the preferred embodiment thereof, occurs in an organic solvent. Suitably, the organic solvent is a C1 to C8 alcohol or C1 to C4 alcohol. Preferably, the alcohol is methanol or ethanol.

The purification of the protonated stabilised diaminophenothiazinium complex (which in one embodiment may be an N-10 protonated stabilised diaminophenothiazinium complex) or stabilised protonated leucomethylene blue complex is preferably by recrystallization.

In one embodiment, the recrystallization is from a solvent selected from the group consisting of water, an alcohol and an ether.

If at least one of the recrystallization solvents is an alcohol then it may be selected from the group consisting of $C_1$ to $C_{10}$ alcohols inclusive of methanol, ethanol, n-propanol and iso-propanol.

If at least one of the recrystallization solvents is an ether it may be tetrahydrofuran or diethyl ether.

Suitably, the oxidising agent of the first aspect, and the preferred embodiment thereof, is a metal-free oxidising agent.

Preferred oxidising agents of the first aspect, and the preferred embodiment thereof, may be selected from the group consisting of oxygen, ozone, chlorine, fluorine, bromine, iodine, hydrogen peroxide, nitric acid and nitrate compounds, phosphoric acid, peroxydisulphuric acid, peroxymonosulphuric acid, sulphuric and sulphurous acids, chlorite, chlorate, perchlorate and other analogous halogen-containing compounds, hypochlorite and other hypohalite compounds, permanganates, nitrous oxide and quinones.

In one embodiment the oxidising agent of the first aspect, and the preferred embodiment thereof, is selected from the group consisting of oxygen and a quinone.

Preferably, the oxidising agent of the first aspect, and the preferred embodiment thereof, is 2,3-dichloro-5,6-dicyano-1,4-benzoquinone (DDQ) or, more preferably, p-benzoquinone.

The stabilised protonated leucomethylene blue complex may be a salt or other ion complex.

In one preferred embodiment, the stabilised protonated leucomethylene blue complex may be a leucomethylene blue:ascorbate complex.

According to a second aspect of the invention there is provided a protonated stabilised diaminophenothiazinium: ascorbate complex.

In one embodiment of the second aspect, the protonated stabilised diaminophenothiazinium complex is a stabilised protonated leucomethylene blue:ascorbate complex.

In one embodiment, the protonated stabilised diaminophenothiazinium complex is an N-10 protonated stabilised diaminophenothiazinium complex.

A third aspect of the invention resides in the protonated stabilised diaminophenothiazinium:ascorbate complex of the second aspect when produced by the process of contacting the diaminophenothiazinium compound with ascorbic acid, or an isomer or salt thereof, to form the protonated stabilised diaminophenothiazinium:ascorbate complex.

In one embodiment of the third aspect, the protonated stabilised diaminophenothiazinium:ascorbate complex is an N-10 protonated stabilised diaminophenothiazinium:ascorbate complex.

In one embodiment of the third aspect, the protonated stabilised diaminophenothiazinium:ascorbate complex is the stabilised protonated leucomethylene blue:ascorbate complex of the second aspect when produced by the process of contacting methylene blue with ascorbic acid to form the stabilised protonated leucomethylene blue:ascorbate complex.

The various conditions for the process of the third aspect may be as described for the first aspect.

According to a fourth aspect of the invention there is provided a use of a protonated stabilised diaminophenothiazinium complex in the purification of a diaminophenothiazinium compound.

In one embodiment, the protonated stabilised diaminophenothiazinium complex is an N-10 protonated stabilised diaminophenothiazinium complex.

In one embodiment of the fourth aspect, the protonated stabilised diaminophenothiazinium complex is a stabilised protonated leucomethylene blue complex used in the purification of methylene blue.

In one embodiment, the stabilised protonated leucomethylene blue complex is a stabilised protonated leucomethylene blue salt.

In one embodiment, the stabilised protonated leucomethylene blue complex is the stabilised protonated leucomethylene blue:ascorbate complex of the second aspect.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

DETAILED DESCRIPTION

The present invention is predicated, at least in part, on the surprising finding that methylene blue can be simply and effectively purified by reducing a post-synthesis or commercially available sample to form a reduced stabilised protonated leucomethylene blue complex, which may be a salt or other ion complex, which can then be purified by, for example, recrystallization before being allowed to oxidise back to methylene blue. Crystallisation of methylene blue itself, as a purification method to remove both Azure type impurities and metal contaminants, has proven to be ineffective on its own in achieving even close to pharmaceutical grade material and so it is particularly surprising that recrystallization of the reduced leucomethylene blue form, even with the close structural similarities to the Azures still remaining, is an effective means for separation of that leucomethylene blue form from both the Azures and metal contaminants. A simple oxidation step then provides the methylene blue but in a highly purified form.

Unless defined otherwise, all technical and scientific terms used herein have the same meaning as would be commonly understood by those of ordinary skill in the art to which this invention belongs.

As used herein, the term "leucomethylene blue" (also referred to herein as 'LMB') refers to the well known N-10 protonated reduced form of methylene blue which may also be referred to as N,N,N',N'-Tetramethyl-10H-phenothiazine-3,7-diamine, which has the chemical formula $C_{16}H_{19}N_3S$, CAS number 613-11-6, and which is shown in the structure below.

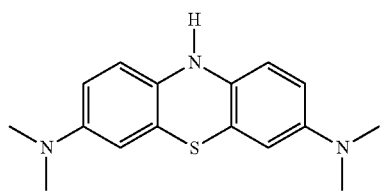

As used herein, the terms "complex", "complexes" and "complexed" refer generally to leucomethylene blue chemically associated with an ion or electrically neutral molecule. The complex may be a salt. While not wishing to be bound to any particular theory, in a preferred embodiment it is believed the complex is a stabilised protonated leucomethylene blue associated with ascorbic acid, or a salt or isomer thereof, which may be referred to as a stabilised protonated leucomethylene blue:ascorbate complex. The nature of the stabilised protonated leucomethylene blue complex may be affected by the process conditions used in the reduction step, including the pH and ionic strength which may influence salt formation.

As used herein, the terms "recrystallization" and "recrystallising" and "crystallisation" and "crystallising" are used interchangeably to refer to the process of dissolving and subsequently crystallising from solution a substance such as methylene blue or, particularly, the stabilised protonated leucomethylene blue complex formed during the reduction step in the present inventive process.

The terms "diaminophenothiazinium compound" and "methylene blue", being a preferred embodiment of the diaminophenothiazinium compound, may be used interchangeably herein when describing elements of the purification process.

The term "reducing sugar", as used herein, refers to any sugar capable of acting as a reducing agent due to a free aldehyde or ketone moiety which may be present on the compound at all times or upon being placed into solution. Preferred reducing sugars are monosaccharides.

The term "sugar acid", as used herein, refers to a monosaccharide presenting a carboxyl group and includes aldonic acids, ulosonic acids, uronic acids and aldaric acids. Preferred aldonic acids include unsaturated lactones such as, for example, ascorbic acid.

The term "reducing agent" as used herein in relation to carbocyclic and/or heterocyclic reducing agents is one which is capable of reducing, for example, methylene blue to leucomethylene blue. Such a term is commonly understood in the field of chemistry and one of skill in the art can readily appreciate various carbocyclic and/or heterocyclic agents capable of serving this function. A reasonably skilled chemist can determine what is and isn't a suitable carbocyclic and/or heterocyclic reducing agent, e.g., by contacting the diaminophenothiazinium compound in solution with an agent and monitoring the reduction (or lack thereof), e.g., spectroscopically, by a visual colour change such as the blue to green change with methylene blue, or evaluating other physical properties, e.g., melting point.

According to a first aspect of the invention, there is provided a process for the purification of a diaminophenothiazinium compound including the steps of:
 (i) contacting the diaminophenothiazinium compound with a carbocyclic or heterocyclic reducing agent to form a protonated stabilised diaminophenothiazinium complex;
 (ii) purifying the protonated stabilised diaminophenothiazinium complex; and
 (iii) contacting the purified protonated stabilised diaminophenothiazinium complex with an oxidising agent to convert it back to the diaminophenothiazinium compound,
 to thereby purify the diaminophenothiazinium compound.

The diaminophenothiazinium compound may be selected from the group consisting of methylene blue, Azure A, Azure B and Azure C.

In one embodiment, the contact with the reducing agent may form an N-10 protonated stabilised diaminophenothiazinium complex which is subsequently purified and oxidised back to the diaminophenothiazinium compound. This is the case when the compound is methylene blue and may be the case for most diaminophenothiazinium compounds with substituents which allow protonation of the N-10 nitrogen upon contact with the reducing agent.

It will be appreciated that the diaminophenothiazinium compound which is purified and that which is the final desired compound may be different. For example, it may be desirable to purify a diaminophenothiazinium compound such as Azure B and once purification is complete to convert this by methylation into methylene blue. Thus, the first aspect explicitly considers interconversion between different diaminophenothiazinium compounds either subsequent to step (iii) or between steps (i) and (ii) or between steps (ii) and (iii).

Therefore, in one embodiment, the process may further include the step of converting the diaminophenothiazinium compound to a second, related diaminophenothiazinium compound.

In one embodiment, the diaminophenothiazinium compound of the first aspect is a compound of formula V, below:

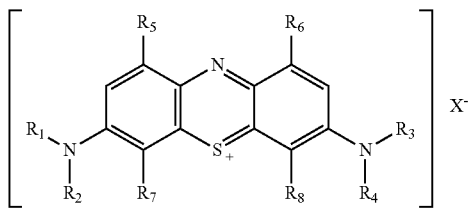

Formula V wherein $R_1$, $R_2$, $R_3$ and $R_4$ are independently selected from hydrogen, $C_1$-$C_6$ alkyl and $C_1$-$C_6$ alkenyl wherein each alkyl or alkenyl group may be substituted with hydroxy, halo or alkoxy;

$R_5$, $R_6$, $R_7$ and $R_8$ are independently selected from hydrogen, nitro, halo, haloalkyl, $C_1$-$C_6$ alkyl and $C_1$-$C_6$ alkenyl; and X is an anionic counterion.

In one embodiment, the alkyl or alkenyl group, if substituted, is substituted with chloro, fluoro, bromo or iodo.

Preferably, $R_1$, $R_2$, $R_3$ and $R_4$ are independently selected from methyl, ethyl, propyl (including n-propyl and isopropyl), butyl (including n-butyl, isobutyl, sec-butyl and tert-butyl), pentyl, iso-amyl and hexyl.

Preferably, $R_5$, $R_6$, $R_7$ and $R_8$ are independently selected from hydrogen, nitro, haloalkyl and $C_1$-$C_4$ alkyl.

Preferably, X is selected from the group consisting of a halide anion, or the conjugate base of a mineral acid such as sulphuric, nitric, hydrochloric and phosphoric acids.

It will be appreciated, and would be understood by one of skill in the art, that the structure encompassed by formula V may also be represented by a number of related resonance structure and tautomeric form representations. For example, a double bond may be not be next to the sulphur and may instead by represented as linking one of the nitrogens to the ring. In this instance the positive charge would not sit on the sulphur atom but rather would be represented on the doubly bonded nitrogen atom. All such resonance and tautomeric structures are explicitly considered to be encompassed by the structure of formula V.

In one preferred embodiment of the first aspect, there is provided a process for the purification of methylene blue including the steps of:
(i) contacting the methylene blue with a carbocyclic or heterocyclic reducing agent to form a stabilised protonated leucomethylene blue complex;
(ii) purifying the stabilised protonated leucomethylene blue complex by recrystallization; and
(iii) contacting the purified stabilised protonated leucomethylene blue complex with an oxidising agent to form methylene blue,
to thereby purify the methylene blue.

The reducing agent of the first aspect, and the preferred embodiment thereof, is a metal-free reducing agent. In embodiments, the term "metal-free" may apply to the reducing reagent itself but not to any salt that may be associated with that reducing agent. For example, "metal-free reducing agent" is considered to include salt forms of otherwise non-metal reducing agents such as sodium ascorbate since the reducing agent, ascorbic acid, does not itself comprise a metal.

Any carbocyclic or heterocyclic reducing agent known in the art to have sufficient reducing power to reduce methylene blue to LMB may be suitable.

In one embodiment, the carbocyclic or heterocyclic reducing agent is a monosaccharide reducing agent.

In embodiments, the heterocyclic reducing agent is selected from a reducing sugar, a sugar acid or a salt of either.

When the reducing agent is a sugar acid, it may be an aldonic acid including ascorbic acid.

Suitable salt forms of the reducing sugar or sugar acid may be selected from sodium, calcium, potassium, magnesium, ammonium and lithium salts.

In certain embodiments, when the reducing agent is a heterocyclic reducing agent it comprises a C5 or C6 oxygen-containing ring. Such ring systems include pyran and furan rings which may be saturated or unsaturated and optionally substituted. Preferred ring systems are reducing sugars, or sugar acids such as ascorbic acid and its isomers.

In embodiments, when the reducing agent is a carbocyclic reducing agent it may comprise a substituted or unsubstituted mono- or bicyclic aromatic ring.

In one embodiment, the carbocyclic reducing agent may comprise a substituted or unsubstituted phenyl ring.

In preferred embodiments, the carbocyclic reducing agent is hydroquinone.

In one embodiment, the reducing agent is a lactone or an isomer or salt thereof. In one particular embodiment, the lactone is an unsaturated lactone or isomer or salt thereof.

In one embodiment, the reducing agent of the first aspect, and the preferred embodiment thereof, is selected from the group consisting of hydroquinone, D-ascorbic acid, L-ascorbic acid, D-isoascorbic acid, L-isoascorbic acid, lactose, fructose, dextrose, xylitol, and salts thereof.

Suitably, the ascorbic acid is L-ascorbic acid or a salt thereof.

It is highly preferred that the reducing agent is ascorbic acid, most preferably L-ascorbic acid since it is postulated that reduction of methylene blue with L-ascorbic acid forms a protonated LMB:ascorbate complex which is particularly stable and which allows for purification by simple recrystallization means. Such a complex may be formed with other analogous reducing sugars or sugar acids.

Preferably, the diaminophenothiazinium compound is contacted with the reducing agent at an acidic pH. More preferably, the diaminophenothiazinium compound is contacted with the reducing agent at below pH 3. Even more preferably, the diaminophenothiazinium compound is contacted with the reducing agent at below pH 1.

The reduced diaminophenothiazinium complex may be a salt. When the reducing agent is ascorbic acid and the diaminophenothiazinium compound is methylene blue then the reduced diaminophenothiazinium complex is a stabilised protonated leucomethylene blue:ascorbate complex.

Purification, generally, is understood by one of skill in the art as a means for removing at least a portion of one or more undesired components (e.g., impurities) from the desired product. In preferred embodiments, the impurities to be removed will be undesired diaminophenothiazinium compounds and/or metal impurities. The improvement in purity may be monitored and measured by various techniques such as chromatography, mass spectrometry and the like.

The purification of the reduced diaminophenothiazinium complex may be achieved by a range of techniques which are known in the art such as chromatography, for example through a column of silica or modified silica or using HPLC, ion-exchange techniques, filtration, washing, recrystallization and others. However, in a highly preferred embodiment, the purification of the reduced diaminophenothiazinium complex is by recrystallization.

Filtration may be used in addition to the recrystallization, particularly to remove metal ions, and can be effected by filtration through metal binding filters, for example filtration supports including silica gel, activated charcoal, neutral, basic or acidic alumina gel, micro porous membranes, resins grafted with metal-capturing groups, and fibres grafted with metal-capturing groups. Metal ions can also be removed by passage through or over any known metal binding absorbent such as silica or diatomaceous earth or other commercial substrate manufactured for the purpose of binding or removing metals.

In one embodiment, the recrystallization is from a solvent selected from the group consisting of water, an alcohol and an ether. It may be preferable that all three solvent classes are used, in varying degrees, for the recrystallization of the LMB complex. In one embodiment, when all three classes of solvents are employed in the recrystallization then they may be used in a ratio of water:alcohol:ether of 1:2-4:6-10, preferably about 1:3:8 on a volume basis.

If at least one of the recrystallization solvents is an alcohol then it may be selected from the group consisting of $C_1$ to $C_{10}$ alcohols or $C_1$ to $C_4$ alcohols inclusive of methanol, ethanol, n-propanol and iso-propanol.

If at least one of the recrystallization solvents is an ether it may be tetrahydrofuran or diethyl ether.

The stabilised protonated leucomethylene blue complex may be a salt or other ion complex.

In one embodiment, the stabilised protonated leucomethylene blue complex may be a stabilised protonated leucomethylene blue:ascorbate complex.

Preferably, the diaminophenothiazinium compound or methylene blue is contacted with the reducing agent at an acidic pH. An acidic environment is required for the reduction reaction to proceed at a useful rate and to produce optimal conversion of the methylene blue to LMB. More preferably, the methylene blue is contacted with the reducing agent at below pH 3. Even more preferably, the methylene blue is contacted with the reducing agent at below pH 1.

The acidic environment may be achieved by the addition of one of a variety of acids such as non-interfering organic acids or mineral acids. Preferably, the reduction solution is made acidic with an acid chosen from the monoprotic and diprotic mineral acids such as hydrochloric, sulphuric, nitric, phosphoric, boric, hydrofluoric, hydrobromic and perchloric. More preferably, the mineral acid is hydrochloric or sulphuric acid. Most preferably, the mineral acid is hydrochloric acid The oxidising agent used to convert the purified LMB complex back into methylene blue is not particularly limited and a wide range of known and commercially available oxidising agents may be suitable for use.

It is well known that leucomethylene blue will oxidise back to methylene blue simply upon standing in a solution which is left exposed to air and it will be apparent to a skilled chemist that any oxidising agent, including air, is suitable for this component of the reaction. A strong oxidising agent may be used but is not required. To indicate that the oxidation has been successful, it is a very simple matter to monitor the reaction for a color change, such as the change from the green leucomethylene blue solution to a blue methylene blue solution, or to follow the reaction by HPLC or mass spectrometry or TLC.

Suitably, the oxidising agent is a metal-free oxidising agent. Metal salts of non-metal containing oxidising agents may be considered to be metal-free as such salt introduced metals are typically well tolerated metals and can often be easily removed by simple metal filtration techniques.

Preferred oxidising agents may be selected from the group consisting of oxygen, ozone, chlorine, fluorine, bromine, iodine, hydrogen peroxide, nitric acid and nitrate compounds, phosphoric acid, peroxydisuphuric acid, peroxymonosulphuric acid, sulphuric and sulphurous acids, chlorite, chlorate, perchlorate and other analogous halogen-containing compounds, hypochlorite and other hypohalite compounds, permanganates, nitrous oxide and a quinone.

In one embodiment the oxidising agent is selected from the group consisting of oxygen and a quinone.

Preferably, the oxidising agent is 2,3-dichloro-5,6-dicyano-1,4-benzoquinone (DDQ) or, more preferably, p-benzoquinone.

In addition to the recrystallization step other purification methods may be used to further purify the reduced stabilised protonated LMB complex. Filtration may be used, particularly to remove metal ions, and can be effected by filtration through metal binding filters, for example filtration supports including silica gel, activated charcoal, neutral, basic or acidic alumina gel, micro porous membranes, resins grafted with metal-capturing groups, and fibres grafted with metal-capturing groups. Metal ions can also be removed by passage through or over any known metal binding absorbent such as silica or diatomaceous earth or other commercial substrate manufactured for the purpose of binding or removing metals.

Preferably in the purification process of the invention, one or more of the steps may be conducted under controlled and stepped temperature conditions. Reactions may also be preferably performed under an inert atmosphere. Solvents, acids and reagents used in the processes are preferably degassed and are ultra pure containing only very low levels of metal ions. All of these measures can assist in stabilising the intermediates, including the reduced stabilised protonated LMB complex and the final methylene blue product, and products of the reaction steps. Particularly, it is beneficial to form the reduced stabilised protonated LMB complex under controlled temperature conditions of 15 to 30° C., more preferably 20 to 25° C. for the period of the en tire reaction. The liquid volume of the reaction is subsequently reduced under vacuum distillation at 35 to 45° C., preferably about 40° C.

Further, purification and drying of the reduced stabilised protonated LMB complex preferably occurs under a nitrogen atmosphere and controlled temperature conditions at 15 to 30° C., preferably 20 to 25° C. In addition, the oxidation of the stabilised protonated LMB complex to convert it back to methylene blue is preferably carried out under stepped temperature conditions between, initially, 5 to 20° C., preferably 10 to 15° C. and, subsequently, 15 to 30° C., preferably 20 to 25° C. and under a nitrogen atmosphere.

A final purification of the so-formed methylene blue by recrystallization may be optionally performed and, if employed, may be carried out under controlled staged temperature conditions of, initially, 50 to 75° C., preferably 60 to 65 CC, followed by a reduction in temperature to 55 to 60° C., followed by cooling to 30 to 50° C., preferably 40 to 45° C. and finally cold conditions of 0 to 5° C. The control of temperature within the limitations described above for the various process steps reduces the formation of various impurities, for example to reduce the likelihood of demethylation, and also optimises yield.

In one embodiment the methylene blue starting material is first passed through a purification step prior to reduction. This may be desirable depending on the purity of the commercially available starting material. Recrystallization from an acidic solution may be suitable.

Thus, in one embodiment of the first aspect, there is provided a process for the purification of methylene blue including the steps of:
  (i) recrystallising the methylene blue from an acidic solution;
  (ii) contacting the recrystallised methylene blue with a carbocyclic or heterocyclic reducing agent to form a stabilised protonated leucomethylene blue complex;
  (iii) purifying the stabilised protonated leucomethylene blue complex by recrystallization;
  (iv) contacting the purified stabilised protonated leucomethylene blue complex with an oxidising agent to form a purified methylene blue; and
  (v) recrystallising the purified methylene blue from an acidic solution,
  to thereby purify the methylene blue.

The various elements and conditions for this embodiment are as previously described, mutatis mutandis, for the first aspect.

Preferably in the purification process of the invention, one or more of the steps may be conducted in an inert atmosphere, such as nitrogen. This can assist in stabilising the intermediates, particularly the reduced stabilised protonated LMB complex, and products of the reaction steps.

In a starting mixture of methylene blue, Azure A, B and C (and other contaminants such as metals), reduction of the methylene blue in the process of the invention to a stabilised protonated LMB complex allows simplified separation from the azures as, in the reduced form, the difference in the chemical properties between the stabilised protonated LMB complex and the Azures has in some manner been amplified. Purification of the stabilised protonated LMB complex enables simplified removal of metal contaminants.

The process described significantly reduces metal ions present, however, if the starting material is particularly high in metal contaminants then the stabilised protonated LMB complex may be further cleaned of any metal contaminants by any of many known processes and then the purified and concentrated complex can be simply converted back to methylene blue.

One of the advantages of the process of the invention over known processes is the simplicity whereby the synthesis of a stabilised protonated LMB complex, which is then subjected to the main purification step, allows purification without the need for the preparation of a complex organic derivative of methylene blue which additional synthesis and deprotection steps often add to residual contamination.

The process of the invention is a reliable and consistent process applicable to any manufacturers "raw" material, for example methylene blue, which substantially reduces metal and organic contaminants as required and provides for a high chemical purity, in an economically viable manner which is applicable on an industrial scale. Reduction of most metals is greater than three fold using the process of the invention, and the final methylene blue product contains less than 3% Azure B and in preferred embodiments provides for less than 2.5% Azure B, by weight, in the final product. The introduction of additional recrystallization steps can reduce the level of Azure B to less than 2%.

Repeating the recrystallization and washing steps can result in even lower levels of contaminants, as can the introduction of any specific metal absorbent technology as an additional step within the process. Similarly too, increasing the amount of water used at this stage can also substantially reduce the Azure levels.

For the process of the invention, any practicable equipment can be used. Preferably non-metallic vessels and equipment is used, such as glass or ceramic or plastic lined equipment, to ensure that additional metal contamination is not introduced.

The resultant purified methylene blue product, after oxidation of the stabilised protonated LMB complex, can be further purified by filtration, recrystallization or other methods as discussed above. In one embodiment of the invention, a methylene blue product is provided comprising (i) from about 2-5 waters of hydration; (ii) a solubility in water of up to about 2%; and (iii) metal levels below the levels specified in the European Pharmacopoeia 5.0. The methylene blue product may further comprise from about 5-25% moisture content.

According to a second aspect of the invention there is provided a protonated stabilised diaminophenothiazinium:ascorbate complex.

In one embodiment, the protonated stabilised diaminophenothiazinium complex is an N-10 protonated stabilised diaminophenothiazinium complex.

In one embodiment of the second aspect, the protonated stabilised diaminophenothiazinium complex is a stabilised protonated leucomethylene blue:ascorbate complex.

The stabilised protonated leucomethylene blue:ascorbate complex has been found to have particularly advantageous properties for use in the process of purification described herein. The stabilised protonated leucomethylene blue:ascorbate complex shows excellent stability and appears to represent a form of stabilised protonated LMB complex which has surprisingly good differentiation from the Azures thereby allowing for excellent purification in a single simple recrystallization step. The need for post-synthesis or other synthetic modification of methylene blue with organic groups is thus avoided. The stabilised protonated leucomethylene blue:ascorbate complex is also formed and then converted back to methylene blue using only simple reagents which are subsequently easily removed without contributing to further impurities within the sample.

A third aspect of the invention resides in the protonated stabilised diaminophenothiazinium:ascorbate complex of the second aspect when produced by the process of contacting the diaminophenothiazinium compound with ascorbic acid to form the protonated stabilised diaminophenothiazinium:ascorbate complex.

In one embodiment of the third aspect, the protonated stabilised diaminophenothiazinium:ascorbate complex is an N-10 protonated stabilised diaminophenothiazinium:ascorbate complex.

In one embodiment of the third aspect, the protonated stabilised diaminophenothiazinium:ascorbate complex is the stabilised protonated leucomethylene blue:ascorbate complex of the second aspect when produced by the process of contacting methylene blue with ascorbic acid or a salt or isomer thereof to form the stabilised protonated leucomethylene blue:ascorbate complex.

The various conditions for the process of the third aspect may be as described for the first aspect.

According to a fourth aspect of the invention there is provided a use of a protonated stabilised diaminophenothiazinium complex in the purification of the diaminophenothiazinium compound.

In one embodiment, the protonated stabilised diaminophenothiazinium complex is an N-10 protonated stabilised diaminophenothiazinium complex.

In one embodiment of the fourth aspect, the protonated stabilised diaminophenothiazinium complex is a stabilised protonated leucomethylene blue complex used in the purification of methylene blue.

In one embodiment, the stabilised protonated leucomethylene blue complex is a stabilised protonated leucomethylene blue salt.

In one embodiment, the stabilised protonated leucomethylene blue complex is the stabilised protonated leucomethylene blue:ascorbate complex of the second aspect.

Although the embodiments exemplified herein relate to the purification of methylene blue, it will be appreciated that, as described for the broad form of the present invention, the inventive concept described may be extended to other diaminophenothiazinium compounds.

The following Example is provided by way of illustration of the invention and is in no way limiting of the scope of the invention.

EXPERIMENTAL

In this Example, a commercially available methylene blue is purified in accordance with the following steps:
Overall Manufacturing Processing Scheme

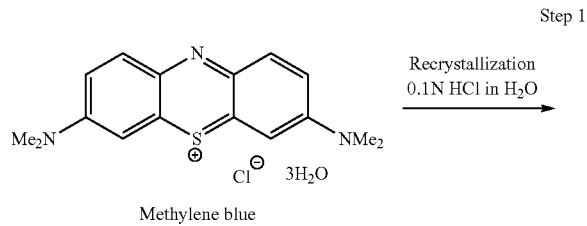

Step 1

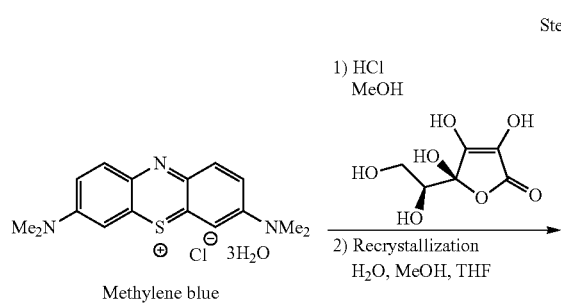

Step 2

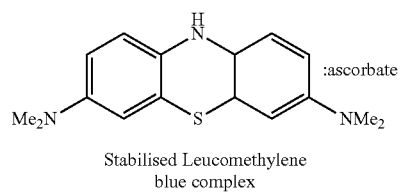

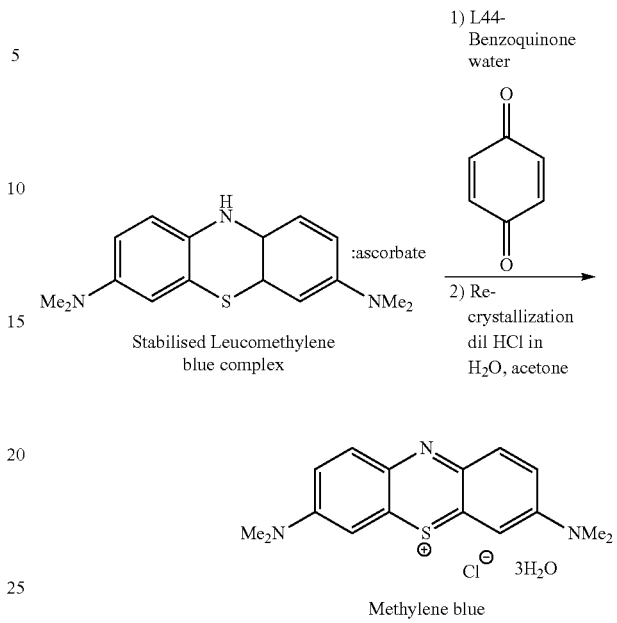

Step 1: Recrystallization of Commercially Available Methylene Blue Starting Material It will be understood that this initial recrystallization step is optional and its use may depend on the purity level of the commercially available starting material. Its use provides optimal results when the starting material contains significant levels of impurities.

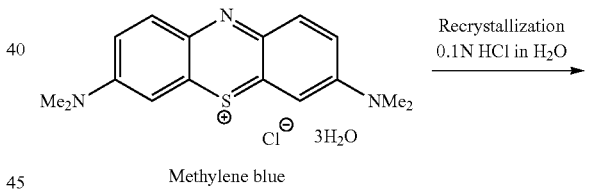

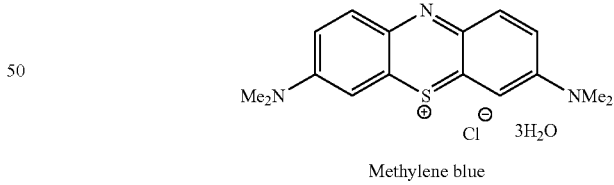

To a glass-lined, closed and jacketed reactor was charged methylene blue (5.5 kg, 1.0 eq.) and sterile purified water (54 kg). Then 0.6 Kg of 31% HCl solution was charged. The batch was adjusted to a temperature of 60 to 65° C. and agitated until dissolution. Next, the batch was cooled over a minimum of 9 hours to 0 to 5° C. The suspension was filtered at 0 to 5° C. and the filtercake was washed with 3.8 kg of cold water (0 to 5 CC), followed by a rinse with 7.3 kg of cold acetone (0 to 5 CC). The filtercake was dried under a flow of nitrogen to give 5.16 Kg of product.

Step 2: Process for Reduction of Methylene Blue to Leucomethylene Blue

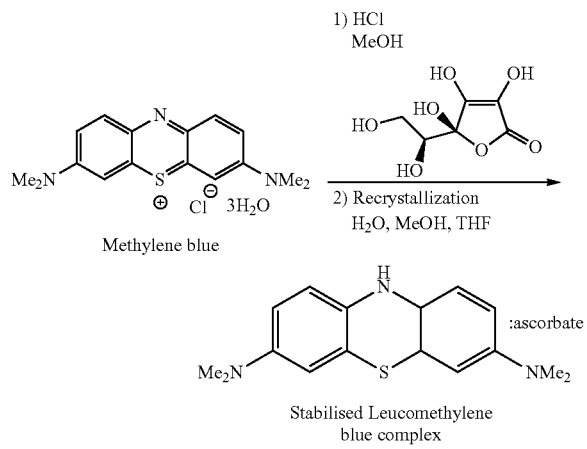

To a 50 L glass-lined reactor was charged 2.8 kg of purified methylene blue from step 1, 1.3 kg of L-ascorbic acid and 32.7 kg of methanol. 1 kg of 31% hydrochloric acid was charged to the batch under $N_2$ with agitation. A rinse of 0.5 kg of methanol was done on the charging equipment to complete transfer. The batch was agitated at 20 to 25° C. for a minimum of 15 minutes. The pH was checked (should be below 1) and the batch was agitated for a minimum of 18 hours. An IPC sample was taken and residual methylene blue with respect to stabilised protonated leucomethylene blue complex in the batch was less than 2%. The batch was then distilled under vacuum to 5.0 to 5.5 parts (14 to 15 L) with respect to the starting methylene blue, while applying an external temperature of NMT 40° C. With agitation, 2.2 kg of water was added and then the temperature of the batch was adjusted to 20 to 25° C. 19.5 kg of THF was added over 1.5 hours with agitation while maintaining the batch temperature of 20 to 25° C. The batch (suspension) was agitated at 20 to 25° C. for a minimum of 16 hours. The suspension was filtered under a constant flow of nitrogen. A mixture of 0.4 Kg of methanol and 4.4 kg of THF (10% MeOH/THF) was used to wash the filtercake, followed by a rinse with 2.5 kg of THF. The cake was dried under a flow of nitrogen to give 1.805 kg of crude stabilised protonated leucomethylene blue complex. A second loop was done on a similar scale and the products from the first and second loop were used in the recrystallization step.

To a 50 L glass reactor was charged 3.3 kg of crude stabilised protonated leucomethylene blue complex, and 3.7 kg of degassed SP water and the mixture was agitated at 20 to 25 CC for 10 to 15 minutes. Then 8.8 kg of degassed methanol was added and the batch was stirred at 20 to 25 CC for 10 to 15 minutes and a solution was confirmed. Next, 26.1 kg of degassed THF was added over a minimum of 1.5 hours. The batch was agitated for a minimum of 24 hours at 20 to 25° C. to complete crystallization. The suspension was filtered under nitrogen atmosphere. A mixture of 0.6 kg of methanol and 5.9 kg of THF (10% MeOH/THF) was used to wash the filtercake, followed by a rinse of 3.2 kg THF. The cake was dried under a flow of nitrogen to give 3.2 kg of light blue to white solid of purified stabilised protonated leucomethylene blue complex.

Step 3: Oxidation of Purified Stabilised Protonated Leucomethylene Blue Complex to Methylene Blue

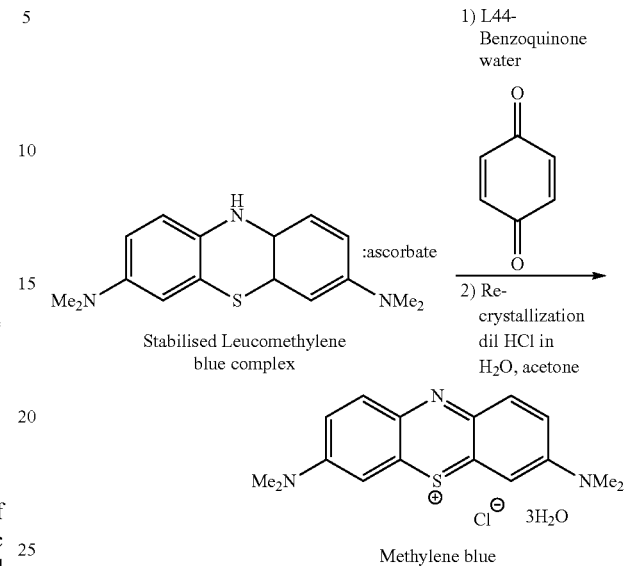

To a 50 L glass reactor was charged 3.2 kg purified leucomethylene blue and 16.1 kg of SP water. The batch was cooled to 10 to 15° C. Via a carboy, a solution of 1 kg p-benzoquinone and 4.1 kg of acetone was added into the batch while keeping the temperature at 10 to 15° C. The carboy was rinsed with 0.9 kg of acetone for complete transfer. The batch was agitated at 10 to 15° C. for 35 minutes and then allowed to warm to 20 to 25° C. and further agitated at this temperature for 5 hours. The batch was sampled for the completion of the reaction by HPLC (typically very little to no leucomethylene blue was detected). With vigorous agitation, 20.2 kg of acetone was added to the mixture and the suspension was stirred at 20 to 25° C. for 5 hours. The suspension was filtered and the filtercake was washed with 6.8 kg of acetone at 20 to 25° C. The filtercake was dried under a flow of nitrogen until transferrable. The solid was transferred back into the 50 L reactor and 25.3 kg of acetone was added and the temperature was adjusted to 20 to 25 CC and the batch was agitated for 3 hours. The suspension was filtered and the filtercake was washed with 7.8 kg of acetone at 20 to 25° C. The filtercake was dried under a flow of nitrogen until transferrable.

Recrystallization

To the 50 L reactor was charged all of the above methylene blue, 43.1 kg of SP water and 34.5 kg of hydrochloric acid solution. The batch was adjusted to 60 to 65 CC and agitated for 10 to 15 minutes. The batch temperature was then adjusted to 55 to 60 CC and the batch was subjected to final clarification filtration at this temperature into a second 50 L reactor. A rinse with 3.4 kg of the HCl solution at 55 to 60° C. was done to complete the filtration. With agitation, the batch was cooled to 40 to 45 CC and 16.3 kg of acetone was charged to the reactor over 30 minutes. The batch was then agitated for 25 minutes at 40 to 45° C. With agitation, the batch was cooled to 0 to 5° C. over a minimum of 8 hours. The batch was further agitated at 0 to 5° C. for 3 hours. The suspension was filtered cold at 0 to 5° C. and the filtercake was washed with 2.1 kg of co Id water (0 to 5° C.), followed by a rinse of 190 kg of cold acetone (0 to 5° C.).

The filtercake was dried under a flow of heated nitrogen to give 3.1 kg of purified methylene blue.

The exemplified process provides the purity data for a series of 3 batches of methylene blue product, purified according to the present process, with purity levels relative to the Azures listed in Table 1. Table 2, below, compares this product to the commercially available methylene blue starting material and to metal impurity levels required by the European Pharmacopoeia.

TABLE 1 levels of the Azure contaminants in three representative batches of methylene blue prepared by the present process.

|  | Batch 1 1305308 | Batch 1 1305309 | Batch 1 1305310 |
|---|---|---|---|
| Azure A &C | 0.2% | 0.2% | 0.1% |
| Azure B | 2.3% | 2.3% | 2.4% |

TABLE 2

Metal contamination limits for methylene blue (European Pharmacopoeia).

| Metal | European Pharmacopoeia Limits (ppm) | Present product (ppm) | Commercial Sample of Methylene Blue (ppm) |
|---|---|---|---|
| Aluminium | 100 | 5.1 | 18 |
| Copper | 300 | 0.14 | 7.4 |
| Iron | 200 | 3.6 | 46 |
| Zinc | 100 | 0.69 | 91 |
| Nickel | 10 | 0.09 | 2.5 |
| Chromium | 100 | 0.91 | 5.0 |
| Molybdenum | 10 | 0.81 | 3.5 |
| Manganese | 10 | 0.09 | 0.81 |
| Tin | 10 | 0.04 | 0.11 |
| Lead | 10 | 0.13 | 0.2 |
| Cadmium | 1.0 | <0.02 | <0.1 |
| Mercury | 1.0 | 0.35 | 1.0 |

It can be seen that in every instance the level of metal impurity is significantly lower than that prescribed as acceptable by the European Pharmacopoeia 5.0 and, in some instances, the level of the metal approaches the limits of detection by standard methods. The combined level of the 3 Azure dye impurities is about 2.5% by weight or less.

Further Testing for the Reduction of Methylene Blue

In the following tests the method requires an equivalent molar concentration to 0.13 g Ascorbic Acid for 0.28 g Methylene Blue in 3.3 g Methanol or an equivalent molar concentration of Water. Water was used as an alternative solute for reducing agents either not soluble in methanol or which are better solubilised in water. All solutions were initially heated to accelerate the potential reaction, then an initial observation, involving visual inspection, was taken. In keeping to the established method of methylene blue purification, an amount of concentrated hydrochloric acid was then added to each solution, mixed thoroughly and left overtime to react. A secondary observation was then recorded. The distinct colour change of methylene blue, from blue to green, observed with addition of ascorbic acid as per the above method demonstrates a chemical reaction in which methylene blue transforms leucomethylene blue and this was used as an indication of successful reduction in the below experiments.

Sodium Ascorbate—to demonstrate that salts of ascorbic acid also work successfully, sodium ascorbate was added to the methylene blue in water, as described above. When sodium ascorbate was added to water with methylene blue it exhibited a colour change similar to the ascorbic acid and methylene blue reaction, except it created a small amount of precipitate. Following the addition of hydrochloric acid the precipitate dissolved and the colour changed further to a lighter shade of green more closely similar to that of ascorbic acid and methylene blue. This demonstrates that sodium ascorbate works in a similar way to ascorbic acid in its reaction with methylene blue, and suggests that other ascorbic salts may have a similar effect on methylene blue.

Hydroquinone—the use of hydroquinone exhibited colour changes in solution with methylene blue in both solutions of water and methanol. The colour changes in both solutions were the classic blue to green, being similar to the colour change in the ascorbic acid and methylene blue solution, suggesting hydroquinone effects a similar reduction with methylene blue as ascorbic acid. Firstly, hydroquinone with methylene blue in methanol exhibited a green colour change around the edges of the hydroquinone crystals, but due to poor dissolution the colour change was not heterogeneous. Hydroquinone with methylene blue in water similarly presented green colouration but due to the gelation of the solution it was unable to properly mix and react so the colour change was not as intense as with ascorbic acid. Nonetheless, hydroquinone has shown that it can reduce methylene blue and it seems likely that either the use of lower concentrations of hydroquinone, to minimise gelation, or the use of a solvent which more readily solubilises hydroquinone, such as propylene glycol or carbon tetrachloride, will lead to better results.

Dextrose, fructose and xylitol—a colour change was observed with these substances; turning from blue to a grey and purple hue which suggests methylene blue has undergone a reduction, albeit not as complete as with ascorbic acid. It may be that a better outcome could be obtained with changes in concentration or solvent.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this patent specification is intended to embrace all alternatives, modifications and variations of the present invention that have been discussed herein, and other embodiments that fall within the spirit and scope of the above described invention.

In the claims which follow and in the preceding description of the invention, except where the context clearly requires otherwise due to express language or necessary implication, the word "comprise", or variations thereof including "comprises" or "comprising", is used in an inclusive sense, that is, to specify the presence of the stated integers but without precluding the presence or addition of further integers in one or more embodiments of the invention.

The invention claimed is:

1. A process for the purification of a diaminophenothiazinium compound including the steps of:
   (i) contacting the diaminophenothiazinium compound with a reducing agent comprising a C5 or C6 oxygen-containing ring to form a protonated stabilised diaminophenothiazinium complex;

(ii) purifying the protonated stabilised diaminophenothiazinium complex; and (iii) contacting the purified protonated stabilised diaminophenothiazinium complex with an oxidising agent to convert it back to the diaminophenothiazinium compound, to thereby purify the diaminophenothiazinium compound, wherein the diaminophenothiazinium compound is a compound of formula V:

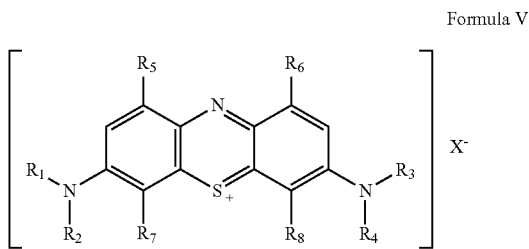

Formula V wherein $R_1$, $R_2$, $R_3$ and $R_4$ are independently selected from hydrogen, $C_1$-$C_6$ alkyl and $C_1$-$C_6$ alkenyl wherein each alkyl or alkenyl group may be substituted with hydroxy, halo or alkoxy;

$R_5$, $R_6$, $R_7$ and $R_8$ are independently selected from hydrogen, nitro, halo, haloalkyl, $C_1$-$C_6$ alkyl and $C_1$-$C_6$ alkenyl; and X is an anionic counterion.

2. The process of claim 1 wherein the protonated stabilised diaminophenothiazinium complex is an N-10 protonated stabilised diaminophenothiazinium complex which is subsequently purified and oxidised to give the diaminophenothiazinium compound.

3. The process of claim 1 wherein the diaminophenothiazinium compound is selected from the group consisting of methylene blue, methylene green, Azure A, Azure B and Azure C.

4. The process of claim 1 wherein when the reducing agent is a monosaccharide reducing agent.

5. The process of claim 1 wherein the reducing agent is a lactone or a salt or isomer thereof.

6. The process of claim 1 wherein the reducing agent is selected from a reducing sugar, a sugar acid or a salt of either.

7. The process of claim 6 wherein the reducing agent is selected from D-ascorbic acid, L-ascorbic acid, D-isoascorbic acid, L-isoascorbic acid, lactose, fructose, dextrose, and salts thereof.

8. The process of claim 7 wherein the reducing agent is L-ascorbic acid or a salt thereof.

9. The process of claim 1 wherein the diaminophenothiazinium compound is contacted with the reducing agent at an acidic pH.

10. The process of claim 1 wherein purification of the protonated stabilised diaminophenothiazinium complex or stabilised protonated leucomethylene blue complex is by a process selected from the group consisting of chromatography, ion-exchange, filtration, washing and recrystallisation.

11. The process of claim 10 wherein the recrystallisation is from a solvent selected from the group consisting of water, an alcohol and an ether.

12. The process of claim 1 wherein the oxidising agent is a metal-free oxidising agent.

13. The process of claim 12 wherein the oxidising agent is selected from the group consisting of oxygen and a quinone.

14. The process of claim 1 wherein the protonated stabilised diaminophenothiazinium complex is a stabilised protonated leucomethylene blue complex in the form of a salt or other ion complex.

15. The process of claim 1 further including the step, prior to step (i), of recrystallising the diaminophenothiazinium compound from an acidic solution.

16. The process of claim 1 further including the step, subsequent to step (iii), of recrystallising the purified diaminophenothiazinium compound from an acidic solution.

* * * * *